Feb. 15, 1949. E. S. BOERNER Plant Pat. 823
ROSE PLANT
Filed May 14, 1947
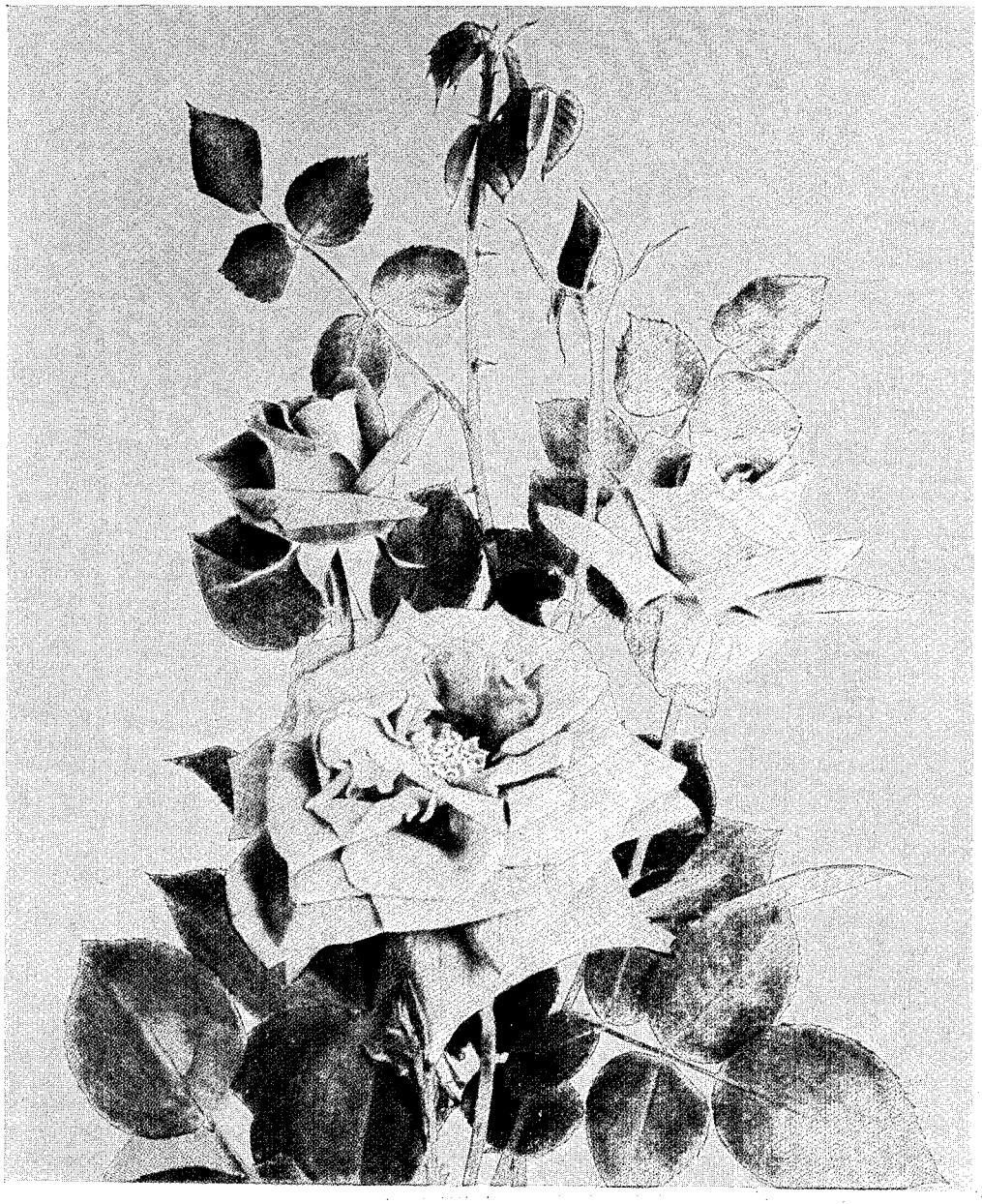
Inventor
E. S. Boerner
By Robb & Robb
Attorneys Patented Feb. 15, 1949

Plant Pat. 823

UNITED STATES PATENT OFFICE

823

ROSE PLANT

Eugene S. Boerner, Newark, N. Y., assignor to Jackson & Perkins Company, Newark, N. Y., a corporation of New York Application May 14, 1947, Serial No. 748,086

1 Claim. (Cl. 47—61)

The present invention relates to a new and distinct variety of hybrid tea rose plant, resulting from the crossing of the variety "Flambeau" (Pl. Pat. #374) and an unidentified "Flambeau" seedling (unpatented).

The dominating distinctions of this new rose reside in the velvety, vibrant deep red color of its flowers, a very much deeper color than the parent "Flambeau"; the high centered form of the flowers with petals which reflex perfectly; and the characteristic strong veining on the inside of the petals.

The bush is a vigorous grower, hardy and extremely free blooming, with foliage (old) having characteristic markings of Oxblood Red color on the under side.

Asexual reproduction of this new variety shows the foregoing characteristics come true to form and are established.

The accompanying drawing illustrates the distinctive characteristics of the flowers at different stages of development and specimens of the young and old foliage.

The following is a detailed description of the new variety, color terminology being in accordance with Ridgway's Color Standard:

Parentage: Seedling.

*Seed parent.*—"Flambeau."

*Pollen parent.*—"Flambeau" seedling.

Classification: Botanic and commercial—hybrid tea.

*Flower*

(Observations made in the fields of Jackson & Perkins Company, Newark, New York, in the month of October.)

Blooming habit: Recurrent—continuous.

Bud:

*Size.*—Large.

*Form.*—Ovoid. Is not affected by wet or hot weather.

*Color.*—When sepals first divide—Oxblood Red, Plate 1; when petals begin to unfurl—Carmine, Plate 1; when half blown—inside of petals—Carmine, Plate 1; reverse of petals—between Rose Red, Plate 12, and Pomegranate Purple, Plate 12.

*Sepals.*—Branched. Curl back when petals begin to unfurl. Color—inside—Kildare Green, Plate 31; outside—Rainette Green, Plate 31.

*Calyx.*—Shape—pear. Size—small. Aspect—smooth. Odor when rubbed—none. Color—Light Bice Green, Plate 17.

*Peduncle.*—Length — medium. Aspect — rough. Color—Light Hellebore Green, Plate 17. Strength—Erect; slender.

*Opening.*—Bud opens up well. Is not affected by adverse weather conditions.

Bloom:

*Size.*—Large. Average size when fully expanded, 4½" to 5".

*Borne.*—Singly, several together.

*Stems.*—Long; strong.

*Form.*—When first open—high center. Permanence—retains its form to the end.

*Petalage.*—Double (full but open center). Number of petals under normal conditions, 35.

*Color.*—Center of flower—Nopal Red, Plate 1. Outer petals—Carmine, Plate 1, overlaid with Rose Red, Plate 12. Base of petals (aiglet)—Sulphur Yellow, Plate 5. Inside of petals—Carmine, Plate 1, overlaid with Rose Red, Plate 12. Reverse of petals—Pomegranate Purple, Plate 12, overlaid with Rose Red, Plate 12. General tonality from a distance—Carmine, Plate 1, overlaid with Rose Red, Plate 12.

*Discoloration.*—General tonality at end of first day—Carmine, Plate 1, overlaid with Rose Red, Plate 12. Second day—Carmine, Plate 1, overlaid with Rose Red, Plate 12. Third day—Nopal Red, Plate 1, overlaid with Rose Red, Plate 12.

Petals:

*Texture.*—Thick. Is not affected by wet or hot weather.

*Appearance.*—Inside—velvety; outside—satiny.

*Form.*—Oval; pointed.

*Arrangement.* — Imbricated (regularly arranged shinglelike). Petaloids in center—few; large.

*Persistence.*—Drop off cleanly.

*Fragrance.* — Moderate. Nature — fruity (Russet apple).

*Lasting quality.*—On the plant and as cut flower—long.

Genital organs:

*Stamens.*—Anthers — medium size; many. Color — Buff Yellow, Plate 4. Arrangement—regular around styles. Filaments (threads)—medium length. Color—Spectrum Red, Plate 1.

*Pollen.*—Maize Yellow, Plate 4.

*Styles.*—Bunched; uneven length; short; heavy.

*Stigmas.*—Maize Yellow, Plate 4.

*Ovaries.*—All enclosed in calyx.

*Plant*

Form: Bush.
Growth: Vigorous; upright.
Foliage: 5 to 7 leaflets.
*Size*—Large.
*Quantity.*—Normal.
*Color.*—New foliage: upper side—Victoria Lake, Plate 1; under side—Oxblood Red, Plate 1. Old foliage: upper side—Dark Cress Green, Plate 31; under side—Hellebore Green, Plate 17, shaded with Oxblood Red, Plate 1.
*Shape.*—Oval pointed.
*Texture.*—Upper side—leathery; under side—smooth. Ribs and veins—ordinary.
*Edge.*—Serrated (saw toothed).
*Serrations.*—Single; small.
*Leaf stems.*—Kronberg's Green, Plate 31. Under side—prickles.
*Stipules.*—Long; bearded.
*Disease resistance*—resistant.
Wood:
*New wood.*—Color—Auburn, Plate 2. Bark—smooth.

*Old wood.*—Color—Cedar Green, Plate 6. Bark—smooth.
Thorns:
*Thorns.*—On main stalks from base—many. On laterals from stalk—ordinary. Form—broad base; medium length; hooked downward.
Color when young—Nopal Red, Plate 1. Position—irregular.
*Prickles.*—On main stalks and on laterals—few. Color—Lettuce Green, Plate 5.
*Short needles.*—On main stalks and on laterals—none.

I claim:

A new and distinct variety of rose plant characterized as to novelty by the color and high center form of the flowers; the reflex development and veining of the petals; vigorous, hardy and extremely free blooming habits of the plant and the red coloring of the under surface of the foliage, substantially as shown and described.

EUGENE S. BOERNER.

No references cited.